(12) United States Patent
Axelrod

(10) Patent No.: US 7,360,504 B2
(45) Date of Patent: Apr. 22, 2008

(54) RADIOPAQUE ANIMAL CHEW

(75) Inventor: Glen S. Axelrod, Colts Neck, NJ (US)

(73) Assignee: T.F.H. Publications, Inc., Neptune City, NJ (US)

( * ) Notice: Subject to any disclaimer, the term of this patent is extended or adjusted under 35 U.S.C. 154(b) by 504 days.

(21) Appl. No.: 10/390,125

(22) Filed: Mar. 17, 2003

(65) Prior Publication Data
US 2004/0137117 A1    Jul. 15, 2004

Related U.S. Application Data

(60) Provisional application No. 60/438,862, filed on Jan. 9, 2003.

(51) Int. Cl.
*A01K 29/00* (2006.01)

(52) U.S. Cl. ..................... 119/709; 426/326

(58) Field of Classification Search ............ 119/709, 119/710, 711, 132, 623, 92, 635, 805, 807; 426/132, 623, 92, 635, 805, 807
See application file for complete search history.

(56) References Cited

U.S. PATENT DOCUMENTS

| | | | |
|---|---|---|---|
| 3,608,555 A | 9/1971 | Greyson | 128/348 |
| 3,645,955 A | 2/1972 | Flynn | 260/31.4 |
| 3,749,134 A | 7/1973 | Slingluff et al. | 138/177 |
| 3,871,334 A | 3/1975 | Axelrod | 119/29.5 |
| 3,901,829 A | 8/1975 | Slingluff et al. | 252/478 |
| 4,282,876 A | 8/1981 | Flynn | 128/349 R |
| 4,513,014 A | 4/1985 | Edwards | 426/132 |
| 4,722,344 A | 2/1988 | Cambron et al. | 128/658 |
| 5,177,170 A | 1/1993 | Sarpeshkar et al. | 528/76 |
| 5,346,981 A | 9/1994 | Sarpeshkar et al. | 528/85 |
| 5,476,069 A | 12/1995 | Axelrod | 119/709 |
| 5,827,565 A | 10/1998 | Axelrod | 426/623 |
| 5,941,197 A | 8/1999 | Axelrod | 119/710 |
| 6,093,427 A | 7/2000 | Axelrod | 426/194 |
| 6,093,441 A | 7/2000 | Axelrod | 426/632 |
| 6,110,521 A | 8/2000 | Axelrod | 426/549 |
| 6,126,978 A | 10/2000 | Axelrod | 426/285 |
| 6,159,516 A | 12/2000 | Axelrod et al. | 426/456 |
| 6,178,922 B1 * | 1/2001 | Denesuk et al. | 119/710 |
| 6,180,161 B1 | 1/2001 | Axelrod | 426/623 |
| 6,190,268 B1 * | 2/2001 | Dewanjee | 473/370 |
| 6,274,662 B1 * | 8/2001 | Lynch et al. | 524/423 |
| 6,623,382 B2 * | 9/2003 | Winskowicz | 473/378 |
| 6,736,141 B2 * | 5/2004 | Freedman | 128/850 |
| 6,827,657 B2 * | 12/2004 | Sullivan | 473/374 |

FOREIGN PATENT DOCUMENTS

| | | |
|---|---|---|
| CA | 2315176 | 6/1999 |
| WO | WO1999/31172 A | 6/1999 |

OTHER PUBLICATIONS

Huberbrite (R) Barium Sulfate Products, Huberbrite (HB) Barium Sulfate Sales Literature, 2002.*
Akrochem Corporation company literature: Mineral Fillers, Huberbrite ® Description, Propeties, Application.*
Huber Engineered Materials Material Safety Data Sheet on Product Name: Barite (Trade Name: HUBERBRITE® Products) Revision Date: Jun. 15, 2001 (pp. 1-5).
Huber Engineered Materials Material Safety Data Sheet on Product Name: Chemically Treated Barite (Trade Name: Huberbrite Interlok ® ) Revision Date: Jun. 15, 2001 (pp. 1-5).
Huber Engineered Materials Material Safety Data Sheet for Product Name: Chemically Treated Barite (Trade Name: Huberbrite® IT) Revision Date: Jun. 15, 2001 (pp. 1-5).
Office Action dated Jun. 29, 2007 issued in the counterpart Chinese Patent Application No. 20040002876.4 (5 pgs).

* cited by examiner

*Primary Examiner*—Yvonne R. Abbott
(74) *Attorney, Agent, or Firm*—Grossman, Tucker, Perreault & Pfleger PLLC

(57) ABSTRACT

An animal chew toy comprising a radiopaque polymer. The radiopaque polymer may comprise a polymer that is inherently radiopaque or a polymer that has been made radiopaque by the addition of an additive that provides radiopaque characteristics. The radiopaque polymers of the present invention may be manufactured by melt processing techniques, such as extrusion, compression and/or injection molding.

1 Claim, No Drawings

RADIOPAQUE ANIMAL CHEW

CROSS-REFERENCE TO RELATED APPLICATIONS

This application claims the benefit of U.S. Provisional Application Ser. No. 60/438,862 filed Jan. 9, 2003.

FIELD OF THE INVENTION

The present invention relates to radiopaque animal chews, and methods for their manufacture, wherein a host polymer suitable for use as an animal chew is made radiopaque. In the event that a portion of the chew becomes inadvertently lodged within the animal, in a life-threatening manner, it can now be more quickly diagnosed and more rapidly treated.

BACKGROUND OF THE INVENTION

Polymeric materials have been widely used for years in both medical and dental applications. Such applications include surgical and body implants and other prosthetic devices, (e.g., heart valves, blood vessels, etc.). In dentistry, for example, polymer materials have been used to produce removable dentures, temporary crown and bridge materials, restorative materials, impression materials, and the like.

It is generally desirable that medical implants be radiographically opaque such that their precise location within the host body can be detected by X-ray examination. In addition, it is advantageous that such medical implant be optically or visually transparent so that a flow of fluid therethrough may be observed. Therefore, a vast amount of prior art has been directed at the preparation of polymeric materials for use in medical or dental applications that can be detected by X-ray analysis.

In the field, however, of animal chew toys, it is certainly the case that a variety of disclosures exist detailing specific resins and specific designs to enhance the attractiveness of the chew toy to an animal. In addition, numerous disclosures exist that attest to the use of specific materials, and specific additives, and specific molding conditions for a chew toy product.

Along such lines, attention is directed to U.S. Pat. No. 3,871,334 to Axelrod, which discloses a chewable object from nylon with a flavor or odor extract. Attention is also directed to U.S. Pat. No. 4,513,014 which sought to provide a more chewable product comprising a polyurethane elastomer again having incorporated therein a flavor or odor extract.

Attention is next directed to Applicant's U.S. Pat. No. 5,827,565 which discloses a process for making a heat expandable dog chew comprised primarily of injection molding potato starch granules and an attractant. Attractants recited include chicken powder, liver powder, ham, turkey, beef and or fish. Vegetable additives such as spinach or carrots also may be added. The resultant mixture is molded under heat and pressure into a desired form, such as a dog bone. The dog bone so produced can be modified in texture or hardness by subsequent heating, preferably in a microwave oven.

In Applicant's U.S. patent application Ser. No. 09/138,804, which was a continuation-in-part of U.S. Pat. No. 5,827,565, there is disclosed a dog chew having natural fruit flavor to increase the dog's appetite for such chew. Such fruit flavored dog chew may also include natural food coloring to enhance the attractiveness of the chew to the dog owner. The food coloring may also correspond to the fruit flavor, and the dog chew disclosed therein may also embody a breath sweetener for a dog such as mint, spearmint, peppermint or wintergreen and may also include parsley. The preferred form of such edible chew maintained the basic ingredient of a heat-expandable starch, such as potato starch. Fruit flavoring may be added to the granules of a mixture of potato starch, water and calcium carbonate along with natural fruit flavorings.

Attention is also directed to the following U.S. patents and copending applications, commonly owned by the assignee herein: U.S. Pat. No. 5,476,069; U.S. patent application Ser. No.: 08/923,070 filed Sep. 3, 1997 entitled "Vegetable Based Dog Chew", now U.S. Pat. No. 6,093,427; Ser. No. 08/738,423 filed Oct. 25, 1997 entitled "Edible Dog Chew", now U.S. Pat. No. 5,827,565; Ser. No. 08/784,834 filed Jan. 17, 1997 entitled "Carrot-Based Dog Chew", now U.S. Pat. No. 5,941,197; Ser. No. 08/888,611 filed Jul. 7, 1997 entitled "Vegetable Dog Chew", abandoned; Ser. No. 09/114,872 filed Jul. 14, 1998 entitled "Heat Modifiable Edible Dog Chew"; Ser. No. 09/138,804 filed Aug. 21, 1998 entitled "Improved Edible Dog Chew", now U.S. Pat. No. 6,126,978; Ser. No. 09/116,070 filed Jul. 15, 1998 entitled "Wheat & Casein Dow Chew With Modifiable Texture", now U.S. Pat. No. 6,110,521; Ser. No. 09/116,555 filed Jul. 15, 1998 entitled "Heat Modifiable Peanut Dog Chew", now U.S. Pat. No. 6,093,441; Ser. No. 09/227,767 filed Jan. 8, 1999 entitled "Method of Molding Edible Starch". In addition to such patents and applications, attention is also directed to the art cited in said patents and applications, as such art relates to the field of molded starch products.

As can therefore be seen upon review of all the above, a number of disclosures exist which point to the importance of the use of radiopaque polymer systems for humans. Such disclosures are directed at monitoring the location of an implant via: X-ray analysis. In addition, a variety of disclosures exist directed an animal chew products.

However, to date, animal chew toys have been made without consideration of X-ray analysis issues, or in effect, chew toys have been made such that they are inherently transparent to X-ray detection, and as such, are not detectable within the animal if such chew toy should be improperly ingested. Accordingly, there has existed a long-standing need to develop and provide an economical process to produce an animal chew toy so that the chew toy can be detected by standard X-ray analysis by trained medical professionals.

In addition, although incidents of ingestion of oversized "chewed-off" sections of plastics are relatively rare compared with other foreign objects ingested by the animal, the occurrence may nonetheless result in a severe medical emergency or even death. The potential severity of such an incident makes it important to facilitate the diagnosis and removal of such foreign bodies, regardless of the fact that such event remains outside normal and reasonable expectations.

What is needed therefore is a material or material combination that can maximize the radiopacity of an animal chew without negatively affecting the physical characteristics of the animal chew. Such chew toy should also remain safe for ingestion and must also preserve the associated chewing experience for the animal.

Therefore, it is one object of this invention to produce an animal chew toy that remains attractive to the animal, providing a healthy and engaging chewing experience, but which if improperly ingested can be detected by X-rays and more rapidly removed from the animal in any life-threatening situation.

More specifically, it is also an object of the present invention to establish critical, safe and effective concentrations of a radiopaque additive in a host polymer resin to provide X-ray detection when present in a sized portion of the chew, such sized portion typical of a "break-off" piece of the chew due to animal chewing action.

SUMMARY OF THE INVENTION

An animal chew toy comprising a radiopaque polymer. The radiopaque polymer may comprise a polymer that is inherently radiopaque or a polymer that has been made radiopaque by the addition of an additive that provides radiopaque characteristics. The radiopaque polymers of the present invention may be manufactured by melt processing techniques, such as extrusion, compression and/or injection molding.

DETAILED DESCRIPTION OF THE PREFERRED EMBODIMENTS

As noted, the present invention is directed at an animal chew toy comprising a radiopaque polymer. The term "radiopaque polymer" is therefore defined as any polymer material, suitable for use as an animal chew, that is either inherently radiopaque, or which can be made radiopaque, upon the suitable addition of a radiopaque additive. Such radiopaque polymer materials are then employed to manufacture an animal chew toy. The term "radiopaque" itself refers to that characteristic wherein the polymer material can be detected by X-ray analysis.

For the first group of polymers suitable for use in the present invention, attention is directed to those polymers that incorporate a structure that is inherently radiopaque. Along such lines, one example includes polymers tat contain a halogen in the polymer backbone. Typical of this approach are those polymers disclosed in U.S. Pat. Nos. 4,722,344, 5,177,170 and 5,346,981, whose teachings are incorporated by reference.

Yet another approach is to disperse X-ray opaque substances, such as barium sulfate, a bismuth halide, or a halogen-containing plasticizer, diol, or other such halogen-containing material, within the polymer. See, for example, Y. Delaviz et al., Polymer Preprints (Polymer Division, Am. Chem. Soc.), 30, 215–216 (1989), and U.S. Pat. Nos. 3,608,555, 3,645,955, 3,749,134, 3,901,829, and 4,282,876, whose teachings are incorporated by reference.

Concerning the use of the preferred additive, barium sulfate, it is preferred that such additive is employed at a concentration that can be detected upon X-ray analysis as associated with, e.g., a 1.0 inch×1.0 inch×1.0 inch (L/W/H) section of polymer material containing such additive. In this regard, it has been found that preferably, the level of barium sulfate is about 0.5–15% by weight, and any increment or any range therein. Accordingly, barium sulfate level can be 0.5%, 0.6%, 0.7%, 0.8%, 0.9%, 1.0% . . . 2.0% . . . 3.0% . . . 4.0% . . . 5.0% . . . 6.0% . . . etc., and up to 15.0% by weight in the host polymer.

In addition, in the context of the present invention, the preferred source of barium sulfate is a product sold under the common chemical name barite, and under the trade name Huberbrite®, which product is sold and distributed by Huber Engineered Materials, Quincy Ill. More specifically, such product is described as a naturally occurring mineral substance consisting of barium sulfate at a concentration of 97–99% by weight, calcium carbonate at 1.0–4.0% by weight and silica at 0.1–1.0% by weight. Typically, the silica is present at a level of about 0.4% by weight, and it should also be noted that the barium sulfate concentration may vary beyond the 97–99% by weight noted above, and fall within the range of 93–99% by weight. In addition, according to the MSDS sheet for Huberbrite®, the product is indicated to be non-hazardous in skin contact, skin absorption and ingestion based upon historical exposure determinations.

Furthermore, it is useful to note that in the context of the present invention, it is not necessary to employ United States Pharmacopia (USP) approved grade barium sulfate, and the use of the preferred Huberbriteg product noted above is sufficient. This therefore results in a very economical and useful process for production of the radiopaque animal chew toys of the present invention.

With regards to a host polymer, preferably, the host polymer is a polyurethane, although any other polymer or material suitable for use as an animal chew may be employed. In that regard, polymers such as nylons can be used, as well as animal chews made from natural or synthetic rubber, thermoplastic elastomers and/or thermoset elastomers, natural polymers such as starch, vegetable matter, casein and/or rawhide material.

The barium sulfate itself is preferably mixed within the aforementioned polymer or material and preferably throughout the chew toy, thereby ensuring that those portions of the chew toy, chewed apart by the animal and ingested, can be detected by X-ray analysis. In that regard, it has been found preferable to combine the barium sulfate, or other appropriate radiopaque additive, into the polymer, by melt compounding techniques (extrusion or injection molding). In a most preferred embodiment, barium sulfate, or the preferred Huberbrite® product noted above, is first extrusion blended into a polymer host at relatively high levels (20–85% by weight and any percentage therebetween or any range therebetween) to produce a polymer concentrate of the barium sulfate additive. For example, barium sulfate is preferably first compounded in an elastomeric polyurethane, at a concentration of about 70% by weight. This compounding is preferably achieved by extrusion blending, in which case pellets of the polyurethane are produced containing 70% barium sulfate. Such polyurethane concentrate is then mixed with additional amounts of polyurethane in the injection molding of the chew toy, to provide a chew toy with a final concentration of, preferably, 0.5–15% by weight, more preferably 5.0% by weight.

In addition, within the broad scope of the present invention, blends of different polymers, at least one of which is radiopaque, are suitable for use herein as an animal chew. Accordingly, one polymer component may be radiopaque, the other polymer component non-radiopaque, and the blend is radiopaque and contains properties sufficient to perform as an animal chew within the broad scope of this invention.

What is claimed is:

1. An animal chew toy capable of providing x-ray detection comprising a starch host polymer material and a radiopaque additive wherein the additive consists essentially of a mixture of barium sulfate, calcium carbonate and silica formed into an animal chew toy, wherein said mixture comprises 93-99% by weight barium sulfate, 1-4% by weight calcium carbonate and 0.1-1.0% silica; wherein said additive mixture is dispersed through out the animal chew toy at a concentration to provide a level of barium sulfate at about 0.5-15% by weight in said host polymer material and provides x-ray detection.

* * * * *